United States Patent
Hwang et al.

(10) Patent No.: US 9,561,492 B2
(45) Date of Patent: Feb. 7, 2017

(54) METHOD FOR PRODUCING LACTIDE DIRECTLY FROM LACTIC ACID AND A CATALYST USED THEREIN

(71) Applicant: KOREA RESEARCH INSTITUTE OF CHEMICAL TECHNOLOGY, Daejeon (KR)

(72) Inventors: Dong Won Hwang, Anyang-si (KR); Jong-San Chang, Dajeon (KR); Pravin P. Upare, Maharastra (IN); U-Hwang Lee, Gyeonggi-do (KR); Young Kyu Hwang, Dajeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 14/869,138

(22) Filed: Sep. 29, 2015

(65) Prior Publication Data

US 2016/0016151 A1    Jan. 21, 2016

Related U.S. Application Data

(62) Division of application No. 14/422,526, filed as application No. PCT/KR2013/003532 on Apr. 24, 2013.

(30) Foreign Application Priority Data

Aug. 20, 2012    (KR) .................. 10-2012-0090883

(51) Int. Cl.

| | | |
|---|---|---|
| *C07D 319/00* | (2006.01) | |
| *B01J 23/14* | (2006.01) | |
| *C07D 319/10* | (2006.01) | |
| *C07D 319/12* | (2006.01) | |
| *B01J 21/04* | (2006.01) | |
| *B01J 21/06* | (2006.01) | |
| *B01J 21/08* | (2006.01) | |
| *B01J 35/00* | (2006.01) | |
| *C01G 19/02* | (2006.01) | |
| *B01J 37/03* | (2006.01) | |
| *B01J 29/03* | (2006.01) | |
| *B01J 29/40* | (2006.01) | |
| *B01J 29/70* | (2006.01) | |

(52) U.S. Cl.
CPC .................. *B01J 23/14* (2013.01); *B01J 21/04* (2013.01); *B01J 21/063* (2013.01); *B01J 21/066* (2013.01); *B01J 21/08* (2013.01); *B01J 29/0308* (2013.01); *B01J 29/405* (2013.01); *B01J 29/7057* (2013.01); *B01J 35/002* (2013.01); *B01J 35/0006* (2013.01); *B01J 37/031* (2013.01); *B01J 37/035* (2013.01); *C01G 19/02* (2013.01); *C07D 319/10* (2013.01); *C07D 319/12* (2013.01)

(58) Field of Classification Search
CPC ....................................... B01J 23/14
USPC ........................................ 549/274
See application file for complete search history.

(56) References Cited

U.S. PATENT DOCUMENTS

| | | | |
|---|---|---|---|
| 5,053,522 A | 10/1991 | Muller | |
| 5,138,074 A * | 8/1992 | Bellis ................... | C07D 319/12 549/267 |
| 5,374,743 A | 12/1994 | Thayer et al. | |

FOREIGN PATENT DOCUMENTS

| | | |
|---|---|---|
| KR | 20080018657 A | 2/2008 |
| KR | 20100124999 A | 11/2010 |

OTHER PUBLICATIONS

Chen, Faming Zhuanli Shenqing Gongkai Shuomingshu (2004), CN 1488628 A 20040414.*
Cao Li, "Study on the Synthesis of Lactide Use Solid Superacid as Catalyst", China Papers, Aug. 2010. Abstract Only.
Naik, B, "A Review on Chemical Methodologies for Preparation of Mesoporous Silica and Alumina Based Materials", Recent Patents on Nanotechnology, Revised May 2009, vol. No. 3 pp. 213-224.
International Search Report Appln. No. PCT/KR2013/003532; Dated Jul. 29, 2013.
USPTO Restriction Requirement U.S. Appl. No. 14/422,526; Dated Jul. 22, 2015.

* cited by examiner

*Primary Examiner* — Nizal Chandrakumar
(74) *Attorney, Agent, or Firm* — Ladas & Parry LLP

(57) ABSTRACT

The present invention provides a method for directly producing lactide by subjecting lactic acid to a dehydration reaction in the presence of a catalyst comprising a tin compound, preferably, a tin (IV) compound, wherein lactide can be produced directly or by one step from lactic acid, without going through the step of producing or separating lactic acid oligomer. The method of the present invention has advantages of causing no loss of lactic acid, having a high conversion ratio to lactic acid and a high selectivity to optically pure lactide, and maintaining a long life time of the catalyst. Further, since lactic acid oligomer is not or hardly generated and the selectivity of meso-lactide is low, the method also has an advantage that the cost for removing or purifying this can be saved.

3 Claims, 1 Drawing Sheet

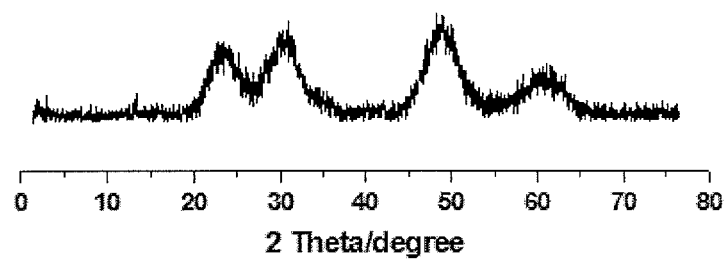

METHOD FOR PRODUCING LACTIDE DIRECTLY FROM LACTIC ACID AND A CATALYST USED THEREIN

TECHNICAL FIELD

The present invention relates to a method for producing lactide directly or via one step from lactic acid, and a catalyst used therein. More particularly, the present invention relates to a method for producing lactide directly or via one step by subjecting lactic acid to a dehydration reaction in the presence of a catalyst comprising a tin compound, and a catalyst comprising the tin compound used for the direct production of lactide.

BACKGROUND ART

Polylactide (PLA) is a polymeric material having optical characteristics, which has been used as a biodegradable or bioabsorbable medical material for surgical suture thread, microcapsules for injection or the like, and recently, is employed as an environmental-friendly biodegradable material which can be used in the production of various high-molecular products such as packaging materials, home appliances, office supplies, vehicle interior materials, or the like.

In order for polylactide to be used for the above usage, it is required to have a high optical purity (D-type or L-type optical isomer) and have high molecular weight. For this, lactide, which is a monomer used for producing polylactide, should have high optical purity and chemical purity.

The following Reaction Chart 1 shows routes for producing lactide from lactic acid or lactic acid ester. In case of using lactic acid as a starting material, lactide can be produced through a course of Route-1/Depolymerization or a course of Route-4. In case of using lactic acid ester as a starting material, lactic can be produced through a course of Route-2 or a course of Route-3/Depolymerization.

[Reaction Chart 1]

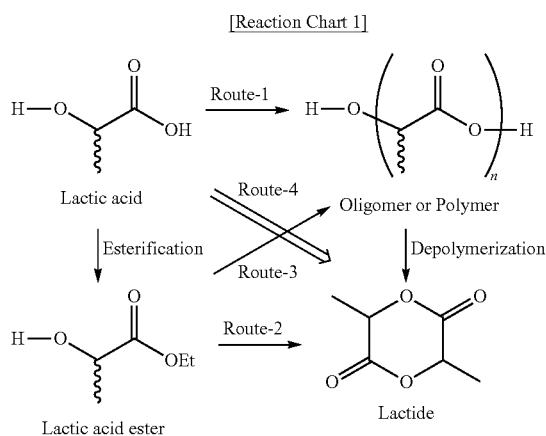

The course of Route-1/Depolymerization is a conventional method for producing lactide by using lactic acid as a starting material, wherein lactide is obtained via a two-step process consisting of firstly polymerizing lactic acid under reduced pressure to produce an oligomer or prepolymer in a molecular weight of about 500~5,000, and then depolymerizing the produced prepolymer with the flow of inert gas under a reduced pressure (U.S. Pat. No. 5,274,073; U.S. Pat. No. 5,247,059; U.S. Pat. No. 5,274,127; U.S. Pat. No. 6,277,951). NatureWorks (a company in USA) commercially produces L-type PLA bioplastic in a scale of about 140 thousand tons a year by a manner consisting of producing lactide from L-type lactic acid via said two-step process, and then subjecting the resulting lactide to a condensation polymerization reaction in a polymerization reactor. Recently, Purac (a company in Netherlands) has also built a plant in Thailand and started a commercial production of lactide via the above two-step reactions.

However, in case of going through the two-step process, the products such as prepolymer and lactide are deteriorated when they reside for a long period of time within the reactor, and thus there is a problem that the amount of byproducts produced such as meso-lactide increases during the production of L-type or D-type lactide. The two-step process of Prepolymerization-Depolymerization of lactic acid has problems that part of the prepolymer or oligomer which is the reactant in the Depolymerization step is not decomposed to lactide and further polymerizes or forms a waste material mixed with the catalyst component included in the prepolymer. Also, the two-step process involves problems that a vacuum pump for making a high vacuum is required and the reaction device is complex to make the device cost high.

The course of Route-2 or Route-3/Depolymerization is a method using lactic acid ester as a starting material. There are several references disclosing a process via Route-2 for the production of lactide directly or by one-step from lactic acid ester, or a process via Route-3 and Depolymerization for the production of lactide through prepolymer from lactic acid (e.g. Korean Patent Application No. 10-2009-0043985, Japanese Patent Laid-Open No. 1999-036366, Japanese Patent Laid-Open No. 1993-286966, and Japanese Patent Laid-Open No. 1994-031175).

Finally, the process via Route-4 relates to a method for producing lactide directly or by one step from lactic acid as a starting material. A method for the production of lactide by this process or a catalyst for the production thereof has ever been suggested, but the suggested method and catalyst have failed to provide satisfactory results in conversion ratio and selectivity when considering the process efficiency.

U.S. Pat. No. 5,332,839 suggested a direct production of lactide by a process via Route-4. For example, it reports that lactide can be produced directly from lactic acid without going through a prepolymer by gasifying lactic acid at a high temperature of at least 200° C. and then reacting it in a fixed layer charged with a solid acid such as $Al_2O_3$. In case of using a solid acid catalyst such as $Al_2O_3$, however, there are limitations such that the productivity of lactic acid oligomer is high, the yield of lactide is low, carbon monoxide is generated by the degradation of lactic acid during the reaction, and the life of the catalyst is short.

U.S. Pat. No. 5,138,074 also suggested a direct production of lactide by a process via Route-4. For example, it discloses an example for producing lactide directly from lactic acid in the presence of SnO. However, it does not disclose results such as conversion ratio of lactic acid, selectivity of lactide, production ratio of oligomer byproduct, and thus it is difficult to refer to the catalyst and reaction in detail.

Many methods for producing lactide by using lactic acid ester as a starting material (Route-2 and Route-3) and methods for producing lactide by a two-step process by using lactic acid as a starting material (Route-1 and Depolymerization) have been developed. The method for producing lactide directly or by one step from lactic acid as a starting material (Route-4) has not been employed in a commercial process due to the absence of a suitable catalyst, although it has an advantage that the process is simple when compared with the two-step process by the Prepolymerization/Depolymerization of lactic acid (Route-1 and Depolymerization).

SUMMARY OF THE INVENTION

Technical Subject

The purpose of the present invention is to develop a catalyst that can be used in a process for producing lactide directly or by one step from lactic acid as a starting material, without going through a step of producing or separating lactic acid oligomer, and a method for the direct production of lactide using the catalyst.

Means for Achieving the Subject

The present inventors conducted researches for several years in order to improve and simplify the process for the production of lactide from lactic acid, and as a result, they found out that lactide can be obtained directly or by one step from lactic acid when lactic acid is subject to dehydration reaction in the presence of a catalyst comprising a tin compound, and thus consummated the present invention.

The method for producing lactide directly or via one step from lactic acid using the catalyst according to the present invention has advantages of causing no loss of lactic acid, having a high conversion ratio to lactic acid and a high selectivity to optically pure lactide, and maintaining a long life time of the catalyst.

Effect of the Invention

The method according to the present invention which can produce lactide directly or by one step from lactic acid without going through the step of producing or separating lactic acid oligomer has advantages of causing no loss of lactic acid, having a high conversion ratio to lactic acid and a high selectivity to optically pure lactide, and maintaining a long life time of the catalyst. Further, since lactic acid oligomer is not or hardly formed or generated and the selectivity of meso-lactide is low, the method also has an advantage that the cost for removing them or for purifying the product can be saved.

BRIEF DESCRIPTION OF THE DRAWINGS

FIG. 1 is an X-ray diffraction spectrum of tin/silicon mixed oxide ($SnO_2/SiO_2$) obtained from Example 1.

EMBODIMENTS FOR CARRYING OUT THE INVENTION

The first purpose of the present invention is to provide a method for producing lactide directly from lactic acid by reacting the lactic acid in the presence of a catalyst comprising a tin compound.

The first purpose of the present invention can be specified by the method comprising:
(Step 1) subjecting lactic acid to a dehydration reaction in a reactor charged with catalyst comprising a tin compound, and
(Step 2) separating lactide obtained in the above step 1.

More particularly, the first purpose of the present invention can be specified by the following steps:
preparing a reactor charged with catalyst;
supplying an aqueous lactic acid solution to the reactor;
subjecting lactic acid to a dehydration reaction and/or cyclodehydration reaction in a reactor charged with the catalyst to form lactide; and
separating lactide resulted from the above step from unreacted lactic acid and water.

In the present invention, a tin compound means a catalyst comprising a tin oxide, an organotin compound or tin salt. Tin salt can include fluoride, chloride, bromide, iodide, oxide, nitride or the like.

According to a preferable embodiment of the present invention, the tin compound can be selected from a tin (IV) compound or mixtures thereof, and the tin (IV) compound can include a tin (IV) oxide ($SnO_2$). The tin oxide can be understood to include a mixture comprising the tin oxide in the form of a mixed oxide or complex oxide.

In the present invention, there is no particular limitation in the content of tin compound in the catalyst. However, the catalyst may comprise the tin compound in an amount of at least 0.1% by weight of the catalyst, in general, at least 1% by weight, particularly, at least 5% by weight, and preferably at least 10% by weight.

According to a preferable modification of the present invention, the tin compound in a catalyst comprising the tin compound can be selected from a tin (IV) oxide ($SnO_2$) or its mixed oxide. Also, a mixed oxide of the tin oxide can mean a mixed oxide of a tin (IV) oxide with an oxide selected from a group consisting of a metal other than tin or a tin (II) oxide.

According to a preferable embodiment of the present invention, the catalyst comprising the tin compound can be a solid catalyst. In the present invention, a solid catalyst means a catalyst which exists in solid or solid matter state without being dissolved in the reaction solution, and stays in an inhomogeneous state (heterogeneous state) with the reaction solution. Liquid phase tin compound carried in a solid metal oxide can be an example of a solid catalyst.

According to an embodiment of the present invention, the catalyst may further comprise an oxide of metal selected from a group consisting of Ti, Al, Zn, Zr, V, Cr, Mn, Fe and Mo, or mixtures thereof. This additional oxide of metal can be added in an amount that the mol ratio of the tin (Sn) compound to additional oxide of metal is generally 1:50~7:1, particularly 1:30~6:1, preferably 1:10~5:1, and more preferably 1:4~4:1.

According to a preferable embodiment of the present invention, the oxide of metal can be used in a form of nano particles or meso particles having a mean particle size of nano size or meso size, and specifically, may be used in a form of a nanoporous or mesoporous molecular sieve. In the present invention, mesoporous molecular sieve can mean a molecular sieve having mesopores having the size of 1~100 nm, particularly 2~50 nm, but are not limited thereto. For example, in case the metal is silicon, it can be selected from a mesoporous silicon oxide selected from a group consisting of SBA-15, MCM-41, Si-BEA, MFI and I-MS, or mixtures thereof, but is not limited thereto.

The second purpose of the present invention is to provide a catalyst used for the direct production of lactide from lactic acid, which comprises a tin compound, preferably tin (IV) compound.

Hereinafter, the method for directly producing lactide from lactic acid of the present invention is explained in detail.

The method for producing lactide directly from lactic acid in the present invention can proceed by a cyclic esterification to obtain lactic acid ester in the form of a stable hexagon dimer by a simultaneous or sequential dehydration of two water molecules from 2 lactic acid molecules.

In the present invention, lactic acid can be generally provided to a reactor or used in the reaction in the form of an aqueous solution of lactic acid. In general, lactic acid is industrially produced by a fermentation method. For example, lactic acid can be obtained in the form of calcium salt or ammonium salt of lactic acid through fermentation in an aqueous solution of monosaccharide such as glucose obtained by saccharification of carbohydrate material consisting of polysaccharide or cellulose, etc. or in the form of an aqueous lactic acid solution through acid fermentation. Then, a purified aqueous solution of lactic acid can be prepared via several purification and concentration steps. There is an advantage that the volume of the reactor can be minimized as the concentration of lactic acid in the aqueous lactic acid solution increases. However, if the concentration of lactic acid gets too high, the viscosity increases, and in this case, there is difficulty in injecting to the reactor by using a liquid pump. Also, in case the concentration of lactic acid is higher than 90%, the production ratio of lactic acid oligomer may increase during the production of lactide. Thus, the concentration of lactic acid in an aqueous solution of lactic acid should be 50~90%, preferably 60~85%.

In the present invention, L-type lactic acid, D-type lactic acid or L-type/D-type mixed lactic acid can all be used as lactic acid.

Next, an aqueous lactic acid solution prepared as above is introduced into a reactor charged with a catalyst and is converted to lactide by a dehydration and/or cyclization reaction. There is no particular limitation in the supply rate of aqueous lactic acid solution, but it can be supplied at a rate of 0.1~3 kg/h per 1 kg of catalyst, particularly at a rate of 0.5~2 kg/h. However, if the supply rate of lactic acid is too high, the conversion ratio of lactic acid decreases, and there is a problem that the costs for separating after the reaction would increase.

When supplying an aqueous lactic acid solution into the reactor, inert gas such as nitrogen, argon, helium or the like can be introduced together with the aqueous solution of lactic acid continuously or intermittently in order to supply the reactant smoothly and/or remove the product quickly. Inert gas facilitates lactide, unreacted lactic acid and any byproduct including water which are resulted after the reaction of lactic acid to be quickly removed from the reactor, and thus, it may be helpful in preventing inactivation of the catalyst and maintaining the life time of the catalyst. The amount of inert gas supplied is 10~300 L/min, particularly 15~250 L/min and preferably 20~200 L/min with respect to 1 kg/h of lactic acid supplied. As the amount of inert gas supplied increases, there are advantages in the supply of the reactant of an aqueous lactic acid solution as well as the remove of lactide, unreacted lactic acid and byproducts including water which are produced during the reaction. However, there is a disadvantage that when the amount exceeds 300 L/min with respect to the supplied amount of 1 kg/h of lactic acid, the cost for introducing gas would increase.

Meanwhile, in order to supply aqueous solution of lactic acid smoothly, a reactor installed with a dispersion plate at the inlet can be used, and in this case, the amount of inert gas required to be injected together with aqueous solution of lactic acid can be reduced.

In the present invention, with regard to reaction temperature, particularly, the dehydration reaction of aqueous solution of lactic acid can be carried out at a temperature of 170~250 (280) ° C., particularly, 180~240 (250° C. In this temperature range, the conversion ratio from lactic acid to lactide is fast, and simultaneously the production of oligomer by the polymerization reaction of lactic acid can be suppressed.

There is no particular limitation in reaction pressure in the present invention. The process of the present invention is characterized by producing lactide even at a normal pressure. This has a great advantage in operating the process when compared to the process by the conventional process of pre-polymerization/depolymerization of lactic acid which requires high vacuum when producing lactide. However, it is possible to carry out the reaction of the present invention even at vacuum condition for the purpose of easily collecting lactide produced after the reaction and unreacted lactic acid. The normal pressure of the present invention means the atmospheric pressure or a pressure of about 1 atm, but 0.8~1.2 atm can also be deemed as normal pressure.

There is no particular limitation in the form of catalyst in the present invention, and the catalyst may have any form that can be charged in a reactor, for example, granule, pellet, injection mold, monolith, honeycomb, thin film or the like, and a proper form can be selected depending on the form of the reactor.

The inventors found that a catalyst comprising a tin compound, preferably a tin (IV) compound, more preferably a tin (IV) oxide ($SnO_2$) is very effective in a reaction directly converting lactic acid to lactide. Further, the inventors found that in case of using the tin (IV) compound together with an oxide of an additional metal selected from a group consisting of Si, Ti, Al, Zn, Zr, V, Cr, Mn, Fe and Mo, the catalyst presented higher conversion ratio of lactic acid and more excellent selectivity of lactide than the case of using a catalyst comprising a tin compound alone. With regard to a catalyst comprising the tin (IV) compound together with the oxide of metal, the mol ratio of the tin compound to the oxide of metal can be selected from 1:50~7:1, and preferably from 1:4~4:1.

With regard to a catalyst comprising tin (IV) compound together with an oxide of metal, the tin compound may be present in a form carried on or mixed with the additional oxide of metal. For example, the tin compound may be present in the form of a mixed oxide of tin (IV) oxide and the additional oxide of metal.

In the present invention, a preferable example of a catalyst comprising a tin (IV) compound and an oxide of metal can include a mixed oxide of tin and silicon ($SnO_2/SiO_2$) or a complex oxide ($Sn_aSi_bO_4$) (wherein, a and b may be selected from an integer of 0 to 2, and a+b=2). Here, the mol ratio of the tin oxide to silicon oxide is 1:50~7:1, preferably 1:4~4:1.

According to an embodiment of the present invention, a catalyst comprising tin oxide and silicon oxide in the form of a mixed oxide (i.e., catalyst comprising tin/silicon mixed oxide) can be prepared by having a tin oxide precursor carried on in silicon oxide or precursor particles thereof. Specifically, the catalyst according to the present invention can be produced by adding a tin compound such as tin chloride ($SnCl_4$) in a beaker containing nano size silica sol and stirring it, separating the resulting precipitates with a filter, drying at about 100° C., and plasticizing at about 450° C. There is no particular limitation in the drying temperature and plasticizing temperature mentioned in the above.

According to the present invention, when producing a catalyst comprising a tin/silicon mixed oxide, it would be advantageous to have the concentration of tin in a reaction solution for producing the catalyst high. Also, preferably, a precipitation method using silica sol of nano size can be used for uniform dispersion of tin. Of course, with regard to the solid catalyst used in the present invention, there is no particular limitation in the particle size of the component in the present invention. In case of using the above method for producing catalyst, a tin-silicon oxide catalyst of high concentration whose mol ratio of the tin to metal is at least 1:1 can be produced without great loss of BET surface area.

An advantage of the present invention is that since the selectivity of meso-lactide is very low, generally 3% or less, preferably 2.5% or less, and specially 2% or less, the necessity for an additional step of purifying the finally resulted product of optically pure D-lactide or L-lactide or for an additional step of removing meso-lactide is reduced greatly. In prior art, the selectivity of meso-lactide may generally reach 10% or above, and thus a purification process or removal process may be essential.

An advantage of the present invention is that lactic acid oligomer is not or hardly produced, and thus the step of removing or separating lactic acid oligomer is not essential in subsequent processes. Thus, the necessity for a lactic acid oligomer separation column is reduced. In prior art, in particular, according to the technology for producing lactide by pre-polymerization/depolymerization of lactic acid (for example, a course via Route-1), lactic acid oligomer having a high boiling point is together produced as a byproduct in addition to the product of lactide. Thus, there is a problem that a separation column for removing lactic acid oligomer must be installed separately in the subsequent processes in addition to the lactic acid/lactide separation column.

A further advantage of the present invention is that lactic acid oligomer is hardly produced even when performing the dehydration reaction of lactic acid at a high temperature of at least 200° C.

The reaction mixture obtained after the dehydration and/or cyclization reaction of lactic acid according to the present invention comprises not only lactide, but also unreacted lactic acid, water and a small amount of oligomer byproducts. Thus, it may go through a step of separating lactide therefrom.

Lactide can be separated by methods such as distillation, recrystallization or solvent extraction, etc. of lactide used in the prior art. Also, a reaction distillation technique combining the step of going through a direct catalyst conversion reaction of lactide from lactic acid and the step of separating the produced lactide from other compounds can be applied.

Also, according to the technology for producing lactide by pre-polymerization/depolymerization of lactic acid (for example, a process via Route-1) in prior art, meso-lactide is generated in more than a little ratio. Thus, it is necessary to remove meso-lactide or purify optically pure L- or D-lactide. However, according to the technology of direct conversion by using the catalyst according to the present invention, the production ratio of meso-lactide is very low, and thus the cost for removing or purifying can be saved.

According to the present invention, lactide is produced from lactic acid directly or by one step without forming or separating lactic acid oligomer. Thus, it has advantages of causing no loss of lactic acid, having a high conversion ratio to lactic acid and a high selectivity to optically pure lactide, and maintaining a long life time of the catalyst, as well as has effects of simplifying the production process, saving the processing cost and increasing production efficiency.

Further, according to the present invention, a separate apparatus and device for removing lactic acid oligomer is not required because lactic acid oligomer is not generated or hardly generated. In addition, since the selectivity of meso-lactide is lower than prior art, the cost for removing this can be saved as well.

The present invention is not limited to the examples described below, and it is obvious to a person having ordinary skill in the art that various corrections and modifications can be made as far as they do not deviate from the idea and scope of the present invention.

Thus, examples of such modification or corrections fall within the scope of the present invention.

EXAMPLES

Example 1

Production of Lactide by Using $SnO_2(80)/SiO_2$ Catalyst 37 g of $SnCl_4 \cdot 5H_2O$ and 13.75 g of silica sol (Ludox, SM30) are introduced into a beaker and stirred, and while maintaining the temperature at 5° C., the pH is adjusted to pH 8 with 0.2 M NaOH. The temperature of the resulting mixture is raised to 70° C. and the mixture is additionally stirred for 4 hours. The resulting precipitate is separated with a filter, dried for 5 hours at 100° C., and finally calcinated at 450° C. for 2 hours to obtain a catalyst comprising 80% by weight of tin oxide and 20% by weight of silica.

The above obtained catalyst sample is analyzed by the X-ray diffraction analysis to shows that peaks corresponding to tin (IV) compound ($SnO_2$) were mainly observed as peaks relating to tin compound confirmed from the X-ray diffraction spectrum (see FIG. 1). Thus, the catalyst synthesized by the above synthesis method is abbreviated as $SnO_2$ (80% by weight; hereinafter, unit is omitted)/$SiO_2$ catalyst.

A fixed layer reactor is charged with 1 g of the $SnO_2(80)/SiO_2$ (20-40 mesh) catalyst produced in the above, maintained at 180° C. under a normal pressure, and provided with 75% L-aqueous solution of lactic acid (Aldrich) at a supply rate of 0.5 g/h simultaneously with nitrogen at a supply rate of 100 ml/min.

Under the above condition, the (dehydration) reaction is continued for 100 hours. Gas chromatography analysis of the product showed that the conversion ratio of L-lactic acid is 88%, the selectivity of L-lactide is 98%, and the selectivity of meso-lactide is 2%, and oligomer of lactic acid are detected on the chromatogram. The above results are shown in Table 1 below.

Example 2

Production of Lactide by Using $SnO_2(80)/SiO_2$ Catalyst

A fixed layer reactor is charged with 1 g of $SnO_2(80)/SiO_2$ catalyst in the same method as Example 1, maintained at 180° C. under a normal pressure, and furnished with 75% L-aqueous solution of lactic acid at a supply rate of 1.0 g/h simultaneously with nitrogen at a supply rate of 200 ml/min.

Under the above condition, the (dehydration) reaction is continued for 200 hours. Gas chromatography analysis of the product showed that the conversion ratio of L-lactic acid is 84%, the selectivity of L-lactide is 98%, the selectivity of meso-lactide is 2%, and the selectivity of lactic acid oligomer is 1% or less. The above results are shown in Table 1 below.

Example 3

Production of Lactide by Using $SnO_2(80)/SiO_2$ Catalyst

A fixed layer reactor is charged with 1 g of $SnO_2(80)/SiO_2$ catalyst in the same method as Example 1, maintained the reactor at 180° C. under a normal pressure, and furnished with 75% L-aqueous solution of lactic acid at a supply rate of 1.5 g/h simultaneously together with nitrogen at a supply rate of 250 ml/m in.

Under the above condition, the (dehydration) reaction is continued for 500 hours. Gas chromatography analysis of the product showed that the conversion ratio of L-lactic acid is 81%, the selectivity of L-lactide is 98%, and the selectivity of meso-lactide is 2%. No lactic acid oligomer is observed in the chromatography. The results are shown in Table 1 below.

Example 4

Production of Lactide by Using $SnO_2(80)/SiO_2$ Catalyst

A fixed layer reactor is charged with 1 g of $SnO_2(80)/SiO_2$ catalyst in the same method as Example 1, maintained at 180° C. under a normal pressure, and furnished with 75% L-aqueous solution of lactic acid at a supply rate of 2.0 g/h simultaneously together with nitrogen at a supply rate of 300 ml/min.

Under the above condition, the (dehydration) reaction is continued for 100 hours. Gas chromatography analysis of the product showed that the conversion ratio of L-lactic acid is 78%, the selectivity of L-lactide is 98%, the selectivity of meso-lactide is 2%, and the selectivity of lactic acid oligomer is 1%. The results are shown in Table 1 below.

Example 5

Production of Lactide by Using $SnO_2(80)/SiO_2$ Catalyst

A fixed layer reactor is charged with 1 g of $SnO_2(80)/SiO_2$ catalyst in the same method as Example 1, maintained at 180° C. under a normal pressure, and furnished with 75% L-aqueous solution of lactic acid is introduced at a supply rate of 1.5 g/h simultaneously together with nitrogen at a supply rate of 300 ml/min.

Under the above condition, the (dehydration) reaction is continued for 100 hours. Gas chromatography analysis of the product showed that the conversion ratio of L-lactic acid is 84%, the selectivity of L-lactide is 97%, the selectivity of meso-lactide is 2%, and the selectivity of lactic acid oligomer is 1%. The results are shown in Table 1 below.

Example 6

Production of Lactide by Using $SnO_2(80)/SiO_2$ Catalyst

A fixed layer reactor is charged with 1 g of $SnO_2(80)/SiO_2$ catalyst in the same method as Example 1, maintained at 240° C. under a normal pressure, and furnished with 75% L-aqueous solution of lactic acid at a supply rate of 1.5 g/h simultaneously together with nitrogen at a supply rate of 300 ml/min.

Under the above condition, the (dehydration) reaction is continued for 100 hours. Gas chromatography analysis of the product showed that the conversion ratio of L-lactic acid is 96%, the selectivity of L-lactide is 97%, the selectivity of meso-lactide is 2%, and the selectivity of lactic acid oligomer is 1%. The results are shown in Table 1 below.

Example 7

Production of Lactide by Using $SnO_2(40)/SiO_2$ Catalyst 13.5 g of $SnCl_4.5H_2O$ and 30 g of silica sol (Ludox, SM30) are introduced into a beaker and stirred, and while maintaining the temperature at 5° C., the pH is adjusted to pH 8 by 0.2 M NaOH. The temperature of the resulting mixture is raised to 70° C. and the mixture is additionally stirred for 4 hours. The resulting precipitate is separated with a filter, dried for 5 hours at 100° C., and calcinated for 2 hours at 450° C. to obtain a catalyst $SnO_2(40)/SiO_2$ comprising 40% by weight of tin oxide and 60% by weight of silica.

A fixed layer reactor is charged with 1 g of the $SnO_2(40)/SiO_2$ (20-40 mesh) catalyst produced in the above, maintained at 180° C. under a normal pressure, and furnished with 75% L-aqueous solution of lactic acid (Aldrich) at a supply rate of 1.5 g/h simultaneously together with nitrogen at a supply rate of 200 ml/min.

Under the above condition, the (dehydration) reaction is continued for 100 hours. Gas chromatography analysis of the product showed that the conversion ratio of L-lactic acid is 51%, the selectivity of L-lactide is 98%, and the selectivity of meso-lactide is 2%. The selectivity of lactic acid oligomer is 0%, that is, oligomer of lactic acid is not detected on the chromatogram. The above results are shown in Table 1 below.

Example 8

Production of Lactide by Using $SnO_2(80)/TiO_2$ Catalyst

A fixed layer reactor is charged with 1 g of $SnO_2(80)/TiO_2$ catalyst in the same method as Example 1, maintained at 240° C. under a normal pressure, and furnished with 75% L-aqueous solution of lactic acid at a supply rate of 1.5 g/h simultaneously together with nitrogen at a supply rate of 250 ml/min.

Under the above condition, the (dehydration) reaction is continued for 100 hours. Gas chromatography analysis of the product showed that the conversion ratio of L-lactic acid is 72%, the selectivity of L-lactide is 92%, and the selectivity of meso-lactide is 2%. The above results are shown in Table 1 below.

Example 9

Production of Lactide by Using $SnO_2(80)/Al_2O_3$ Catalyst

A fixed layer reactor is charged with 1 g of $SnO_2(80)/Al_2O_3$ catalyst in the same method as Example 1, maintained at 180° C. under a normal pressure, and furnished with 75% L-aqueous solution of lactic acid at a supply rate of 1.5 g/h simultaneously together with nitrogen at a supply rate of 250 ml/min.

Under the above condition, the (dehydration) reaction is continued for 100 hours. Gas chromatography analysis of the product showed that the conversion ratio of L-lactic acid is 66%, the selectivity of L-lactide is 89%, and the selectivity of meso-lactide is 2%. The above results are shown in Table 1 below.

Example 10

Production of Lactide by Using $SnO_2(80)/ZrO_2$ Catalyst

A fixed layer reactor is charged with 1 g of $SnO_2(80)/ZrO_2$ catalyst in the same method as Example 1, maintained at 180° C. under a normal pressure, and furnished with 75% L-aqueous solution of lactic acid at a supply rate of 1.5 g/h simultaneously together with nitrogen at a supply rate of 250 ml/min.

Under the above condition, the (dehydration) reaction is continued for 100 hours. Gas chromatography analysis of the product showed that the conversion ratio of L-lactic acid is 66%, the selectivity of L-lactide is 90%, and the selectivity of meso-lactide is 2%. The above results are shown in Table 1 below.

Example 11

Production of Lactide by Using $SnO_2(100)$ Catalyst 37 g of $SnCl_4.5H_2O$ is introduced into a beaker and stirred, and while maintaining the temperature at 5° C., the pH is adjusted to pH 8 with 0.2 M NaOH. The temperature of the resulting mixture is raised to 70° C. and the mixture is additionally stirred for 4 hours. The resulting precipitate is separated with a filter, dried for 5 hours at 100° C., and calcinated for 2 hours at 450° C. to obtain a catalyst $SnO_2(100)$.

A fixed layer reactor is charged with 1 g of the $SnO_2(100)$ (20-40 mesh) catalyst produced in the above, maintained at 180° C. under a normal pressure, and furnished with 75% L-aqueous solution of lactic acid at a supply rate of 1.5 g/h simultaneously together with nitrogen at a supply rate of 200 ml/min.

Under the above condition, the (dehydration) reaction is continued for 100 hours. Gas chromatography analysis of the product showed that the conversion ratio of L-lactic acid is 48%, the selectivity of L-lactide is 95%, the selectivity of meso-lactide is 3%, and the selectivity of lactic acid oligomer is 2%. The above results are shown in Table 1 below.

Example 12

Production of Lactide by Using $SnO_2(80)/SBA-15$ Catalyst

A fixed layer reactor is charged with 1 g of $SnO_2(80)/SBA-15$ catalyst in the same method as Example 1, maintained at 240° C. under a normal pressure, and furnished with 75% L-aqueous solution of lactic acid at a supply rate of 1.5 g/h simultaneously together with nitrogen at a supply rate of 250 ml/min.

Under the above condition, the (dehydration) reaction is continued for 100 hours. Gas chromatography analysis of the product showed that the conversion ratio of L-lactic acid is 96%, the selectivity of L-lactide is 98%, and the selectivity of meso-lactide is 2%. The above results are shown in Table 1 below.

Comparative Example 1

Production of Lactide by Using $SiO_2$ 35 g of silica sol (Ludox, SM30) is introduced into a beaker and stirred, and while maintaining the temperature at 5° C., the pH is adjusted to pH 8 with 0.2 M NaOH. The temperature of the resulting mixture is raised to 70° C. and the mixture is additionally stirred for 4 hours. The resulting precipitate is separated with a filter, dried for 5 hours at 100° C., and calcinated for 2 hours at 450° C. to obtain a catalyst $SiO_2$.

A fixed layer reactor is charged with 1 g of the $SiO_2$ (20-40 mesh) catalyst produced in the above, maintained at 180° C. under a normal pressure, and furnished with 75% L-aqueous solution of lactic acid at a supply rate of 1.5 g/h simultaneously together with nitrogen at a supply rate of 200 ml/min.

Under the above condition, the (dehydration) reaction is continued for 100 hours. Gas chromatography analysis of the product showed that the conversion ratio of L-lactic acid is 16%, the selectivity of L-lactide is 95%, the selectivity of meso-lactide is 2%, and the selectivity of lactic acid oligomer is 3%. The results are shown in Table 1 below.

Comparative Example 2

Production of Lactide by Using $Al_2O_3$

A fixed layer reactor is charged with 1 g of gamma-$Al_2O_3$ (20-40 mesh) as a catalyst, maintained at 180° C. under a normal pressure, and furnished with 75% L-aqueous solution of lactic acid at a supply rate of 1.0 g/h simultaneously together with nitrogen at a supply rate of 200 ml/min.

Under the above condition, the (dehydration) reaction is continued for 100 hours. Gas chromatography analysis of the product showed that the conversion ratio of L-lactic acid is 29%, the selectivity of L-lactide is 95%, the selectivity of meso-lactide is 2%, and the selectivity of lactic acid oligomer is 3%. The results are shown in Table 1 below.

Comparative Example 3

Production of Lactide by Using $SiO_2(87)/Al_2O_3(13)$

A fixed layer reactor is charged with 1 g of $SiO_2(87)/Al_2O_3$ (13) (20-40 mesh) as a catalyst, maintained at 180° C. under a normal pressure, and furnished with 75% L-aqueous solution of lactic acid at a supply rate of 1.0 g/h simultaneously together with nitrogen at a supply rate of 200 ml/min.

Under the above condition, the (dehydration) reaction is continued for 100 hours. Gas chromatography analysis of the product showed that the conversion ratio of L-lactic acid is 35%, the selectivity of L-lactide is 94%, the selectivity of meso-lactide is 3%, and the selectivity of lactic acid oligomer is 3%. The results are shown in Table 1 below.

Comparative Example 4

Production of Lactide by Using SnO

A fixed layer reactor is charged with 1 g of SnO (20-40 mesh) as a catalyst, maintained at 180° C. under a normal pressure, and furnished with 75% L-aqueous solution of lactic acid at a supply rate of 1.0 g/h simultaneously together with nitrogen at a supply rate of 200 ml/min.

Under the above condition, the (dehydration) reaction is continued for 100 hours. Gas chromatography analysis of the product showed that the conversion ratio of L-lactic acid is 55%, the selectivity of L-lactide is 82%, the selectivity of meso-lactide is 3%, and the selectivity of lactic acid oligomer is 15%. The results are shown in Table 1 below.

TABLE 1

| Example | Conversion ratio of lactic acid (%) | Selectivity of L-lactide (%) | Selectivity of meso-lactide (%) | Selectivity of lactic acid oligomer (%) |
|---|---|---|---|---|
| Example 1 | 88 | 98 | 2 | 0 |
| Example 2 | 84 | 98 | 2 | 1 |
| Example 3 | 81 | 98 | 2 | 0 |
| Example 4 | 78 | 98 | 2 | 1 |
| Example 5 | 84 | 97 | 2 | 1 |
| Example 6 | 96 | 97 | 2 | 1 |
| Example 7 | 51 | 98 | 2 | 0 |
| Example 8 | 72 | 92 | 2 | 6 |
| Example 9 | 66 | 89 | 2 | 9 |
| Example 10 | 66 | 90 | 2 | 8 |
| Example 11 | 48 | 95 | 3 | 2 |
| Example 12 | 96 | 98 | 2 | 0 |
| Comparative example 1 | 16 | 95 | 2 | 3 |
| Comparative example 2 | 29 | 95 | 2 | 3 |
| Comparative example 3 | 35 | 94 | 3 | 3 |
| Comparative example 4 | 55 | 82 | 3 | 15 |

Referring to table 1, it can be understood that the conversion ratio of lactic acid is remarkably low, 40% or below, and the selectivity of lactic acid oligomer is relatively high in case of using $SiO_2$, $Al_2O_3$ and $SiO_2/Al_2O_3$ as catalyst as in comparative examples 1-3. In case the conversion ratio of lactic acid is low, there is a problem that the cost for separating the lactide product from lactic acid after the reaction is very high. Considering that the lactic acid material takes a large part in the method for producing lactide, it can be understood that there are limitations in using the catalyst used in comparative examples 1-3 in the method for directly producing lactide from lactic acid.

Meanwhile, as can be seen from comparative example 4, in case of using only tin (II) compound (SnO) as a catalyst, it can be understood that the selectivity of lactic acid oligomer, which is a byproduct, is high and the optical selectivity of lactide is very low, when compared with the case of using tin (IV) compound ($SnO_2$).

Experimental Example 1

Continuous Production of Lactide by Using $SnO_2(80)/SiO_2$ Catalyst

A fixed layer reactor is charged with 1 g of $SnO_2(80)/SiO_2$ catalyst in the same method as Example 1, and then 75% L-aqueous solution of lactic acid is introduced to the reactor simultaneously with nitrogen. The temperature of the reactor charged with catalyst is maintained at 240° C. and the pressure of the reactor is maintained at normal pressure. The reaction is performed for 3,000 hours at the above condition, while controlling the supply speed of lactic acid and the amount of nitrogen.

Gas chromatography analysis of the product showed that the conversion ratio of L-lactic acid is at least 96%, the selectivity of L-lactide is at least 97%, the selectivity of meso-lactide is 2% or less, and the selectivity of the lactic acid oligomer is 1% or less.

Experimental example 1 shows that the catalyst according to the present invention can maintain excellent catalyst performance for at least 3,000 hours even at very high reaction temperature of 240° C.

The invention claimed is:

1. A solid catalyst comprising a tin component for the direct production of lactide from lactic acid, wherein said tin component is $SnO_2$, or $SnO_2$ and a metal oxide, wherein the metal is selected from the group consisting of Si, Ti, Al, Zn, and mixtures thereof.

2. The catalyst according to claim 1, wherein said metal oxide is contained in an amount that the molar ratio of the tin component to said metal oxide is selected from 1:50 to 7:1.

3. The catalyst according to claim 2, wherein said metal oxide is a mesoporous silicon oxide selected from the group consisting of SBA-15, MCM-41, Si-BEA, MFI and HMS, or mixtures thereof.

* * * * *